United States Patent
Jaynes et al.

(10) Patent No.: US 10,017,542 B2
(45) Date of Patent: Jul. 10, 2018

(54) ANTIMICROBIAL PEPTIDES AND METHODS OF USE THEREOF

(71) Applicant: Riptide Bioscience, Inc., Vallejo, CA (US)

(72) Inventors: Jesse Jaynes, Auburn, CA (US); L. Edward Clemens, Sacramento, CA (US); Henry W. Lopez, Napa, CA (US); George R. Martin, Rockville, MD (US); Kathryn Woodburn, Saratoga, CA (US)

(73) Assignee: Riptide Bioscience, Inc., Vallejo, CA (US)

( * ) Notice: Subject to any disclaimer, the term of this patent is extended or adjusted under 35 U.S.C. 154(b) by 0 days.

(21) Appl. No.: 15/078,794

(22) Filed: Mar. 23, 2016

(65) Prior Publication Data
US 2016/0296594 A1     Oct. 13, 2016

Related U.S. Application Data

(60) Provisional application No. 62/137,206, filed on Mar. 23, 2015.

(51) Int. Cl.
| | | |
|---|---|---|
| *C07K 14/00* | (2006.01) | |
| *A61K 38/16* | (2006.01) | |
| *A61K 45/06* | (2006.01) | |
| *A61K 38/00* | (2006.01) | |
| *C07K 7/06* | (2006.01) | |
| *C07K 7/08* | (2006.01) | |

(52) U.S. Cl.
CPC ............. *C07K 14/00* (2013.01); *A61K 45/06* (2013.01); *C07K 7/06* (2013.01); *C07K 7/08* (2013.01); *A61K 38/00* (2013.01)

(58) Field of Classification Search
CPC ........ A61K 45/06; A61K 38/00; C07K 14/00; C07K 7/08; C07K 7/06
See application file for complete search history.

(56) References Cited

U.S. PATENT DOCUMENTS 7,803,755 B2    9/2010   Jaynes
2002/0155132 A1*   10/2002   Jaynes ................... A61K 38/04
                                          424/208.1

FOREIGN PATENT DOCUMENTS

WO       WO 95/28832 A1 *   11/1995  ............. A61K 38/10

OTHER PUBLICATIONS

Water, from http://www.biology-online.org/dictionary/Water, pp. 1-3, accessed Apr. 24, 2014.*
Wang, Human Antimicrobial Peptides and Proteins, Pharmaceuticals, 2014, 7, pp. 545-594.*
Isaacs et al, A Lipid-Peptide Microbicide Inactivates Herpes Simplex Virus, Antimicrobial Agents and Chemotherapy, 2004, 48, pp. 3182-3184.*
Antibacterial protein PR-39 precursor-Sus scrofa, from https://www.ncbi.nlm.nih.gov/protein/NP_999615.1, pp. 1-3, accessed Jun. 2, 2017.*
Stover et al, Screening Antimicrobial Peptides In Vitro for Use in Developing Transgenic Citrus Resistant to Huanglongbing and Citrus Canker, J. Amer. Soc. Hort. Sci., 2013, 138, pp. 142-148.*
Ma et al., Inhibitory activity of synthetic peptide antibiotics on feline immunodeficiency virus infectivity in vitro, J Virol. Oct. 2002;76(19):9952-61.
Schwab et al., In vitro activities of designed antimicrobial peptides against multidrug-resistant cystic fibrosis pathogens, Antimicrob Agents Chemother. Jun. 1999;43(6):1435-40.
Visser et al., A transient expression assay for the in planta efficacy screening of an antimicrobial peptide against grapevine bacterial pathogens, Lett Appl Microbiol. Jun. 2012;54(6):543-51.
Yates et al., LHRH-conjugated lytic peptides directly target prostate cancer cells, Biochem Pharmacol. Jan. 1, 2011;81 (1):104-10.

* cited by examiner

*Primary Examiner* — Julie Ha
*Assistant Examiner* — Li N Komatsu
(74) *Attorney, Agent, or Firm* — Glenn J. Foulds; Bozicevic, Field & Francis LLP

(57) ABSTRACT

Aspects of the present invention relate to peptides having antimicrobial activity. In certain aspects, the invention relates to peptides having potent antimicrobial activity, broad-spectrum antimicrobial activity, and/or the ability to kill otherwise antibiotic-resistant microbes, or microbes protected by biofilms.

36 Claims, 1 Drawing Sheet

ANTIMICROBIAL PEPTIDES AND METHODS OF USE THEREOF

CROSS-REFERENCE TO RELATED APPLICATIONS

Pursuant to 35 U.S.C. § 119 (e), this application claims the benefit of priority to U.S. Provisional Patent Application Ser. No. 62/137,206, filed Mar. 23, 2015, the disclosure of which application is hereby incorporated by reference herein in its entirety.

GOVERNMENT RIGHTS

This invention was made with Government support under contract 1R434EY024463-01 awarded by the National Institutes of Health and contract DM140274 awarded by the Department of Defense. The Government has certain rights in the invention.

FIELD OF THE INVENTION

The invention generally relates to peptides having antimicrobial activity. More particularly, the invention relates to peptides having potent antimicrobial activity, broad spectrum anti-bacterial activity, and/or the ability to kill otherwise antibiotic-resistant bacteria, or bacteria protected by biofilms.

BACKGROUND OF THE INVENTION

Antibiotic resistance is a major health problem. In part this is attributed to the widespread use of antibiotics not only in medicine, but in agriculture and animal husbandry. Such overuse, while killing susceptible organisms, has also created a powerful selection bias toward antibiotic resistant bacteria. The resulting strains pose a particular problem for individuals with weakened immune systems. In addition, they represent an increasingly serious problem for patients in hospitals.

In addition to exhibiting inherited antibiotic resistance, many emerging bacterial strains can exist in complex associations known as biofilm. The structure of the biofilm constitutes a physical barrier to antibiotic exposure. Biofilms can form in and on tissues, particularly on chronic wounds and medical implants, such as indwelling catheters, artificial organs, and the like, where they have the potential to cause systemic infections requiring heroic treatments. There is an urgent need for materials that are active against antibiotic resistant organisms in both free and biofilm form.

As part of their natural defense against bacteria, many organisms, including insects, amphibians, mammals, and humans, produce antimicrobial peptides. Such peptides are chemically diverse. Some appear to act by penetrating the bacterial cell membrane and destroying it. Others affect bacterial cellular processes. Considerable selectivity is observed, with many of the peptides targeting bacteria in preference to host cells. Unfortunately, host produced antimicrobial peptides are not capable of effectively eliminating a wide range of microbial agents, including many antibiotic resistant bacterial strains. Antimicrobial peptides capable of augmenting the host's antimicrobial defenses are therefore desirable.

SUMMARY OF THE INVENTION

In certain embodiments, the invention provides antimicrobial peptides. The peptides can have anti-bacterial, anti-fungal, and/or anti-protozoal activity. The peptides can have the ability to kill microbial strains that are resistant to conventional antibiotics. In certain embodiments, antimicrobial peptides of the invention are capable of killing microbes (e.g., bacteria) growing as a microbial biofilm.

In certain embodiments, antimicrobial peptides of the invention have amphipathic structure coupled with an overall cationic charge, hydrophobicity, volume, and mass that generates affinity for specific microbial membrane regions. Thus, the antimicrobial peptides can include at least one amphipathic region. The amphipathic region can include a cationic surface suitable for binding to a bacterial membrane. The antimicrobial peptides can include two amphipathic regions linked together by a third region, such as a bubble region or a beta-turn. In certain embodiments, the two amphipathic regions can dimerize, either as a heterodimer or homodimer. Exchange of various domains from one peptide to another or duplication of domains in the peptides is envisioned in the invention to enhance activity, pharmacodynamics or similar features important to clinical application.

The antimicrobial peptides of the invention comprise amino acid residues. In certain embodiments, the amino acid residues are naturally occurring L-amino acid residues. In some embodiments, one or more amino acid residues in an antimicrobial peptide may be a non-naturally occurring amino acid residue, a D-amino acid residue, and/or a beta amino acid residue. In certain embodiments, antimicrobial peptides of the invention have a sequence that is resistant to proteolysis. For example, the peptides can include amino acid residues, either naturally or non-naturally occurring, that confer protease resistance.

In certain embodiments, the antimicrobial peptides have specificity for non-mammalian cells. For example, the peptides can be $10^2$, $10^3$, $10^4$, $10^5$ times, or more effective at killing target microbial cells as compared to killing host mammalian (e.g., human) cells. Some antimicrobial peptides of the invention are active on one type of microbial organism but not on others, thus providing antimicrobial selectivity. For example, certain peptides of the invention can kill antibiotic-resistant target bacteria while having minimal impact on other strains of bacteria, particularly symbiotic bacteria (e.g., bacteria that normally reside in the lumen of the gut of a mammal, such as a human).

In some embodiments, the invention provides compositions, particularly pharmaceutical compositions, which include one or more antimicrobial peptides of the invention. Such compositions can be formulated for oral administration, parenteral administration, topical administration, or the like. Compositions formulated for oral delivery can, for example, include an enteric coat, to ensure that antimicrobial peptides contained therein reach the intestine and beyond. Compositions formulated for topical delivery can be, for example, suspended in a gel or crème or infused into a bandage, to extend the duration of action of the antimicrobial peptides contained therein. Alternatively, the antimicrobial peptides of the invention can be coated on the surface of medical devices, such as surgical instruments and indwelling medical devices (e.g., pacemakers, catheters, artificial joints, and the like), as a means of preventing infection.

In some embodiments, the invention provides methods of treating microbial infections, or prophylactically preventing such infections. The methods can include administering a composition containing one or more antimicrobial peptides of the invention. The compositions can be administered orally, parenterally, topically, or the like. Oral or parenteral administration can be used to treat, for example, systemic infections. Topical administration can be used to treat, for example, wounds or burns. For treatment of patients that require an indwelling medical device, such as a catheter or artificial joint, the treatment can include applying one or more antimicrobial peptides to the medical device prior to inserting the medical device into the patient. The methods can be used to treat any of a wide range of animals, particularly mammals, such as human, domesticated animals, farm animals, zoo animals, wild animals, and the like.

DETAILED DESCRIPTION OF THE INVENTION

Figure 1:
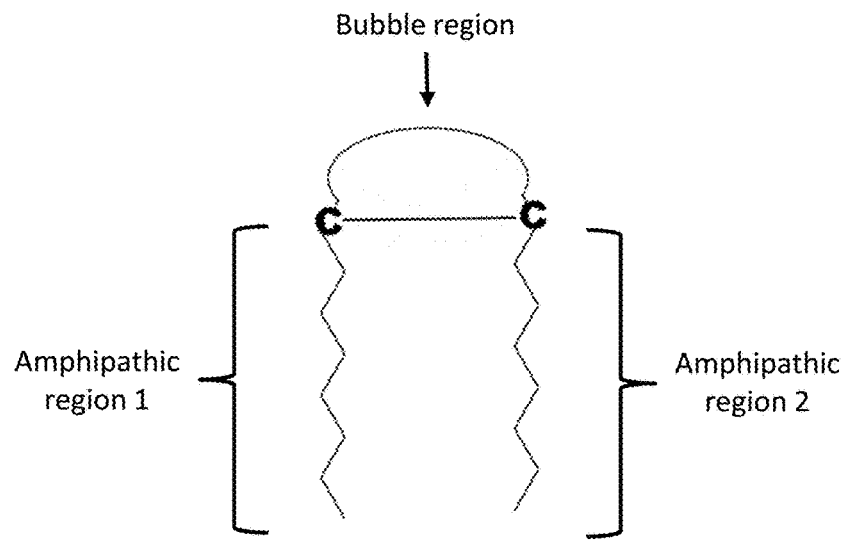
FIG. 1 shows a diagram of a hairpin peptide according to one aspect of the invention.

As discussed above, the invention disclosed herein relates to antimicrobial polypeptides and methods of administering such antimicrobial polypeptides to a subject to prevent or treat a microbial infection.

Before the present invention is described in greater detail, it is to be understood that this invention is not limited to particular embodiments described, which as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The terms "peptide" and "polypeptide" are used synonymously herein to refer to polymers constructed from amino acid residues.

The term "amino acid residue," as used herein, refers to any naturally occurring amino acid (L or D form), non-naturally occurring amino acid, or amino acid mimetic (such as a peptoid monomer).

The "length" of a polypeptide is the number of amino acid residues linked end-to-end that constitute the polypeptide, excluding any non-peptide linkers and/or modifications that the polypeptide may contain.

A "linker" or "linker sequence" can be any moiety that links two peptide sequences together. In some embodiments, a linker is an amino acid sequence that is co-linear with the peptide sequences being linked together, whereas in other embodiments a linker is a separate moiety that is attached to the two peptide sequences, e.g., via a covalent linkage. Linkers can be amino acid sequences or be non-amino acid moieties. In certain embodiments, a linker is used to facilitate dimerization of two amphipathic regions.

Hydrophobic amino acid residues are characterized by a functional group ("side chain") that has predominantly non-polar chemical properties. Such hydrophobic amino acid residues can be naturally occurring (L or D form) or non-naturally occurring. Alternatively, hydrophobic amino acid residues can be amino acid mimetics characterized by a functional group ("side chain") that has predominantly non-polar chemical properties. Conversely, hydrophilic amino acid residues are characterized by a functional group ("side chain") that has predominantly polar (charged or uncharged) chemical properties. Such hydrophilic amino acid residues can be naturally occurring (L or D form) or non-naturally occurring. Alternatively, hydrophilic amino acid residues can be amino acid mimetics characterized by a functional group ("side chain") that has predominantly polar (charged or uncharged) chemical properties. Examples of hydrophilic and hydrophobic amino acid residues are shown in Table 1, below. Suitable non-naturally occurring amino acid residues and amino acid mimetics are known in the art. See, e.g., Liang et al. (2013), "An Index for Characterization of Natural and Non-Natural Amino Acids for Peptidomimetics," PLoS ONE 8(7):e67844.

Although most amino acid residues can be considered as either hydrophobic or hydrophilic, a few, depending on their context, can behave as either hydrophobic or hydrophilic. For example, due to their relatively weak non-polar characteristics, glycine, proline, and/or cysteine can sometimes function as hydrophilic amino acid residues. Conversely, due to their bulky, slightly hydrophobic side chains, histidine and arginine can sometimes function as hydrophobic amino acid residues.

TABLE 1

Hydrophobic and Hydrophilic Amino Acid Residues

| Hydrophilic Residues (X) | Hydrophobic Residues (Y) |
|---|---|
| Arginine | Tryptophan |
| Histidine | Phenylalanine |
| Lysine | Tyrosine |
| Aspartic Acid | Isoleucine |
| Glutamic Acid | Leucine |
| Asparagine | Valine |
| Glutamine | Methionine |
| Pyrrolysine | Cysteine |
| Ornithine | Threonine |
|  | Serine |
|  | Alanine |
|  | Proline |
|  | Glycine |
|  | Selenocysteine |
|  | N-formylmethionine |
|  | Norleucine |
|  | Norvaline |

As described in further detail below, aspects of the present disclosure include antimicrobial peptides having at least one amphipathic region having a specific degree of cationic charge. In certain embodiments, the antimicrobial peptide includes a tail region (e.g., a hydrophobic tail sequence). In certain embodiments, an antimicrobial peptide (or peptide agent) includes two or more amphipathic regions. In such embodiments, two amphipathic regions of an antimicrobial peptide (or peptide agent) are in the form of a dimer, where the two amphipathic regions can have the same or different amino acid sequences (i.e., be homodimer or a heterodimer). In certain embodiments, the two (or more) amphipathic regions are connected via a linker. The linker can be a contiguous (or in-line) amino acid sequence or a non-amino acid moiety as desired by a user. The linker can be, e.g., a bubble region or a beta-turn region. In certain embodiments, the antimicrobial peptide includes a polyproline helix structure.

Exemplary antimicrobial peptide sequences are shown below. Additional antimicrobial peptides could be readily designed by one skilled in the art by combining different regions of the exemplary antimicrobial peptides in different ways as described herein.

Amphipathic Region

By amphipathic region is meant a peptide region that possesses both hydrophobic and hydrophilic elements or characteristics, for example, a peptide region possessing a hydrophilic surface and a hydrophobic surface. A peptide region is said to be in an amphipathic conformation when it exhibits an amphipathic characteristic, which is often dependent on the conditions under which the peptide was made and/or to which it has been subjected. To be considered amphipathic, a peptide sequence (or portion thereof) need not be in the amphipathic conformation at all times. Rather, it is sufficient that the amphipathic conformation be present at least 50%, 60%, 70%, 80%, or more of the time.

In certain embodiments, an amphipathic region of an antimicrobial peptide of the invention can be from 5 to 35 amino acid residues in length, with at least 25% (e.g., 30%, 40%, 50%, 55%, 60%, 65%, 70%, 75%, 80%, or more) of the amino acid sequence of the amphipathic region exhibiting amphipathy. In certain embodiments, an amphipathic region can include an alternating sequence of 1 to 3 hydrophobic and 1 to 3 hydrophilic amino acid residues. An amphipathic region can thus be represented by the formula $(X_{1-3}Y_{1-3})_n$, where X signifies a hydrophilic amino acid residue, Y signifies a hydrophobic amino acid residue, and n is an integer from 2 to 15. For example, an amphipathic region can have a sequence according to Formula 1, Formula 2 (the reverse of Formula 1), or Formula 3:

XYYXXYYXXYYXXYYXXYY        Formula 1:

YYXXYYXXYYXXYYXXYYX        Formula 2:

XYXYXYXYXYXYXYX            Formula 3:

Each hydrophobic amino acid residue Y is selected from the group consisting of a naturally occurring hydrophobic amino acid, a non-naturally occurring hydrophobic amino acid, and a hydrophobic amino acid mimetic. Each hydrophilic amino acid residue X is selected from the group consisting of a naturally occurring hydrophilic amino acid, a non-naturally occurring hydrophilic amino acid, and a hydrophilic amino acid mimetic. Often, the amphipathic conformation will be associated with a particular secondary structure, such as a helical structure. Thus, the amphipathic region of an antimicrobial polypeptide can have an amphipathic $3_{10}$-helical conformation, an amphipathic α-helical conformation, an amphipathic π-helical conformation, or an amphipathic polyproline helical conformation. Alternatively, the amphipathic region of an antimicrobial polypeptide can have an amphipathic β-strand conformation.

In certain embodiments, the amphipathic region of an antimicrobial peptide according to aspects of the present disclosure includes one or more (e.g., 2, 3, 4, 5, 6, 7, 8, 9, 10 or more) large hydrophobic amino acid residues. Examples of large hydrophobic amino acid residues include tryptophan, phenylalanine, and tyrosine. In addition, under certain circumstances, histidine or arginine can be considered a large hydrophobic amino acid residue. In certain embodiments, the amphipathic region of an antimicrobial peptide according to aspects of the present disclosure includes one or more (e.g., 2, 3, 4, 5, 6, 7, 8, 9, 10 or more) small hydrophobic amino acid residues. Examples of small hydrophobic residues include glycine, alanine, serine, cysteine, valine, threonine, and proline. In certain embodiments, the antimicrobial polypeptide has an amphipathic region that includes a combination of large and small hydrophobic residues.

Specific examples of amphipathic regions include:

```
RVFKKAFRKFKKLFKRAF;      (SEQ ID NO: 1)

FARKFLKKFKRFAKKFVR;      (SEQ ID NO: 2)
and

FKRKIKAKLRFKAKVRLK.      (SEQ ID NO: 3)
```

Cationic Charge/Surface

Antimicrobial polypeptides according to aspects of the present disclosure include an amphipathic region having a cationic surface. In certain embodiments, the amphipathic region has a cationic charge (i.e., charge>0, e.g., +1, +2, +3, +4, +5, +6, +7, +8, +9, +10 or more). Thus, in certain embodiments, an amphipathic region of the disclosed peptides contains one or more polar cationic amino acid residues (i.e., having positively charged side chains). Examples of amino acid residues having positively charged side groups (assuming physiological conditions) includes lysine, typically arginine, and sometimes histidine. Accordingly, an antimicrobial polypeptide can have an amphipathic region that includes from 1 to 20 cationic amino acid residues. Thus, an antimicrobial peptide of the invention can include polar amino acid residues, at least 40% (e.g., 50%, 60%, 70%, 80%, 90%, or 100%) of which are cationically charged (e.g., Arg, Lys, His).

Tail Region

In certain embodiments, an antimicrobial peptide includes a tail region. A tail region of an antimicrobial peptide of the invention can be from 3 to 15 amino acid residues in length, with at least 50% (e.g., 60%, 70%, 75%, 80%, 85%, 90%, or more) of the amino acid residues in the tail region being hydrophobic. The tail region can be located at either the N-terminus, the C-terminus, or both termini of the antimicrobial peptide. In certain embodiments, the tail region includes one polar amino acid for every 6 amino acids. An example of a tail region sequence is shown in Formula 4, where Y signifies hydrophobic amino acid residues.

$$YYYYY \qquad \text{Formula 4:}$$

Specific examples of antimicrobial peptides according to aspects of the invention that include a tail region having the sequence FAFAF (SEQ ID NO: 4) include (the tail region is underlined):

```
FAFAFRVFKKAFRKFKKLFKRAF;   (SEQ ID NO: 5)
and

FARKFLKKFKRFAKKFVRFAFAF.   (SEQ ID NO: 6)
```

Bubble Region

In certain embodiments, an antimicrobial peptide includes a bubble region. A "bubble" region of an antimicrobial peptide of the invention consists of a stretch of amino acid residues flanked by a Cysteine residue (C) at each end (see FIG. 1). The stretch of amino acid residues between the cysteine residues can be from 2 to 10 amino acid residues in length, and can be composed of any combination of hydrophobic and hydrophilic amino acids. Bubble regions can link two amphipathic regions and contribute to the formation of a hairpin secondary structure by the antimicrobial peptide (see FIG. 1). This region can thus be classified as a type of "linker region" (as can other regions, described elsewhere herein). In certain embodiments, the hairpin secondary structure can significantly enhance antimicrobial activity.

A bubble region can have, for example, a sequence as shown in Formula 5, where Y signifies hydrophobic amino acid residues and X signifies hydrophilic amino acid residues.

$$C(Y/X)(Y/X)(Y/X)(Y/X)C \qquad \text{Formula 5:}$$

Specific examples of antimicrobial peptides of the invention that include a bubble region having the sequence CLGRFC (SEQ ID NO: 7) include:

```
KIRAKLCLGRFCIRAKLR;      (SEQ ID NO: 8)
and

KIKARLCLGKFCIKARLK.      (SEQ ID NO: 9)
```

Dimerization

Without intending to be limited by theory, it is believed that efficacy of the antimicrobial peptides of the invention depends, in large part, on peptide dimerization and clustering on the cell membrane of the target microbe (e.g., bacterial cell). It is believed that dimers are more efficient at penetrating and, ultimately, lysing the cell membrane. The formation of such dimers can be thermodynamically more favorable when the peptides are physically linked together, e.g., using linker regions. Linker regions can include additional amino acid residues (e.g., like the bubble region described above) or be non-amino acid-containing linker moieties.

Beta Turn Region

A β-turn sequence can be used to physically link individual monomers, making intra-molecular interactions more likely to take place. This appears to be particularly important for amphipathic lytic peptides, as it allows their hydrophobic surfaces to be protected from the aqueous phase. The β-turn sequence allows for two intra-chain amphipathic regions to form a dimer in an antiparallel orientation. This region can thus be classified as a type of "linker region" (as can other regions, described elsewhere herein). For example, a monomer of SEQ ID NO: 6 (shown above) killed greater than 2 logs of Staphylococcus aureus at a concentration of 1.26 µM, while the dimer of SEQ ID NO: 12 (shown below) killed greater than 2 logs of the same bacterium at a concentration less than 0.156 µM. (See Example 5).

A β-turn sequence can be any β-turn sequence known in the art. A β-turn sequence can have, for example, a sequence as shown in SEQ ID NO: 10, where Y signifies hydrophobic amino acid residues and X signifies hydrophilic amino acid residues (i.e., any amino acid residue).

```
(Y/X)GPGR(Y/X)         (SEQ ID NO: 10)
```

Specific examples of antimicrobial peptides of the invention that include a β-turn sequence having the sequence FGPGRF (SEQ ID NO: 11) include:

```
                                          (SEQ ID NO: 12)
FAFAFKAFKKAFKKFKKAFKKAFGPGRFAKKFAKKFKKFAKKFAKFAFAF
```

Polyproline Helix Secondary Structure

Without intending to be limited by theory, it is believed that a helical structure in which a proline residue is repeated, resulting in approximately 3.0 amino acid residues per turn rather than the more normal 3.6 amino acid residues per turn, can result in extended half-life for the resulting peptide. Such helices can be formed, while maintaining the necessary structural features set forth above, including an amphipathic region, cationic charge, and optionally a tail region.

Examples of Antimicrobial Peptides

Examples of antimicrobial peptides according to aspects of the invention are provided below in Table 2. These examples are representative, and not meant to be limiting to the scope of the invention. The "O" residues in the sequences listed below represent the amino acid ornithine.

TABLE 2

Examples of antimicrobial peptides

| RP # | SEQ ID | Amino Acid Sequence |
|---|---|---|
| Na | SEQ ID NO: 1 | RVFKKAFRKFKKLFKRAF |
| Na | SEQ ID NO: 2 | FARKFLKKFKRFAKKFVR |
| Na | SEQ ID NO: 3 | FKRKIKAKLRFKAKVRLK |
| Na | SEQ ID NO: 5 | FAFAFRVFKKAFRKFKKLFKRAF |
| Na | SEQ ID NO: 6 | FARKFLKKFKRFAKKFVRFAFAF |
| Na | SEQ ID NO: 8 | KIRAKLCLGRFCIRAKLR |
| Na | SEQ ID NO: 9 | KIKARLCLGKFCIKARLK |
| RP-433 | SEQ ID NO: 12 | FAFAFKAFKKAFKKFKKAFKKAFGPGRFAKKFAKKFKKFAKKFAKFAFAF |
| RP-434 | SEQ ID NO: 13 | FAKKFAKKFKKFAKKFAKFAFAFGPGRFAFAFKAFKKAFKKFKKAFKKAF |
| RP-435 | SEQ ID NO: 14 | MGFKLRAKIKVRLRAKIKL |
| RP-436 | SEQ ID NO: 15 | CVOLFPVOLFPC |
| RP-437 | SEQ ID NO: 16 | CKLRFRGPGRIKVRLC |
| RP-438 | SEQ ID NO: 17 | CPGFAKKFAKKFKKFAKKFAKFAFAF |
| RP-439 | SEQ ID NO: 18 | KIRAKLCLGRFCIRAKLR |
| RP-440 | SEQ ID NO: 19 | KKKPKPPYLPKPKPPPFFPPKLPPKI |
| RP-441 | SEQ ID NO: 20 | FAFAFKAFKKAFKKFKKAFKKAFGPC |
| RP-442 | SEQ ID NO: 21 | FAFAFAFKKAFKKFKKAFKKAF |
| RP-443 | SEQ ID NO: 22 | FAFAFOAFOOAFOOFOOAFOOAF |
| RP-444 | SEQ ID NO: 23 | FAOOFAOOFOOFAOOFAOFAFAF |
| RP-445 | SEQ ID NO: 24 | FAKKFAKKFKKFAKKFAFAFAF |
| RP-500 | SEQ ID NO: 25 | RLARIVGGFAOOFAOOFOOFAOOFAOFAFAF |
| RP-501 | SEQ ID NO: 26 | CRLARIVCGGFAOOFAOOFOOFAOOFAOFAFAF |

TABLE 2-continued

Examples of antimicrobial peptides

| RP # | SEQ ID | Amino Acid Sequence |
|---|---|---|
| RP-504 | SEQ ID NO: 27 | FOIOAOLGGCLGOFCGGIOAOLOF |
| RP-505 | SEQ ID NO: 28 | OLOSLLKTLSOAOOOOLOTOOOAISO |
| RP-507 | SEQ ID NO: 29 | ALWMTLOOOVLOAOAOALNAVLVGANA |
| RP-508 | SEQ ID NO: 30 | AFAFTAOOOFAOFOAOFANFAFAGFNA |

Accordingly, the invention further provides polypeptides that include an amino acid sequence that is least 50% identical (e.g., at least 60%, 70%, 80%, 90%, 95%, 98%, 99% or more identical) to any one of the antimicrobial polypeptides disclosed herein and still retain at least one antimicrobial property. In certain embodiment, such polypeptide sequences include an amphipathic region having a cationic charge as described in detail above. Moreover, such polypeptides may include additional structural features as described herein, including: a bubble region, a beta-turn region, a polyproline helix structure, a tail, amphipathic region dimer, etc.

As such, in certain embodiments, the invention provides polypeptides that include an amino acid sequence having from 1 to 10 amino acid differences (e.g., 10 or fewer, 9 or fewer, 8 or fewer, 7 or fewer, 6 or fewer, 5 or fewer, 4 or fewer, 3 or fewer, 2 or fewer, or 1 amino acid difference) to any one of the antimicrobial polypeptides disclosed herein and still retain at least one antimicrobial property. An "amino acid difference" as used herein includes: an amino acid substitution, an amino acid insertion, a terminal amino acid addition, an amino acid deletion, a terminal amino acid truncation, or any combination thereof. A substituted amino acid residue (or residues) can be unrelated to the amino acid residue being replaced (e.g., unrelated in terms or hydrophobicity/hydrophilicity, size, charge, polarity, etc.), or the substituted amino acid residue can constitute similar, conservative, or highly conservative amino acid substitution. As used herein, "similar," "conservative," and "highly conservative" amino acid substitutions are defined as shown in Table 3, below. The determination of whether an amino acid residue substitution is similar, conservative, or highly conservative is based exclusively on the side chain of the amino acid residue and not the peptide backbone, which may be modified to increase peptide stability, as discussed below.

TABLE 3

Classification of Amino Acid Substitutions

| Amino Acid in Subject Polypeptide | Similar Amino Acid Substitutions | Conservative Amino Acid Substitutions | Highly Conservative Amino Acid Substitutions |
|---|---|---|---|
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T, K | A | n/a |
| Methionine (M) | L, I, V, F | L, I, V | L, I |
| Valine (V) | I, L, M, T, A | I, L, M | I |

TABLE 3-continued

Classification of Amino Acid Substitutions

| Amino Acid in Subject Polypeptide | Similar Amino Acid Substitutions | Conservative Amino Acid Substitutions | Highly Conservative Amino Acid Substitutions |
|---|---|---|---|
| Leucine (L) | M, I, V, F, T, A | M, I, V, F | M, I |
| Isoleucine (I) | V, L, M, F, T, C | V, L, M, F | V, L, M |
| Phenylalanine (F) | W, L, M, I, V | W, L | n/a |
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K, O* | R, K, O | R, K, O |
| Lysine (K) | R, H, O | R, H, O | R, H, O |
| Arginine (R) | K, H, O | K, H, O | K, H, O |

*"O" represents Ornithine.

Compositions

The present disclosure provides compositions that include an antimicrobial polypeptide as described herein. For example, the antimicrobial polypeptide can be any of the polypeptides listed in Table 2 or a fragment or variant thereof that retains antimicrobial activity. In certain embodiments, the antimicrobial polypeptide included in the compositions of the invention will be a synthetic polypeptide (e.g., made by chemical synthesis and/or produced recombinantly).

The compositions of the invention can include a single antimicrobial polypeptide, or combinations of different antimicrobial polypeptides. The compositions can be substantially free of proteins and other polypeptides. As used herein, the term "substantially free of proteins and other polypeptides" means that less than 5% of the protein content of the composition is made up of proteins and other polypeptides that are not an antimicrobial polypeptide of the invention. A composition that is substantially free of non-antimicrobial polypeptides of the invention can have less than 4%, 3%, 2%, 1%, 0.5%, 0.1%, 0.05%, 0.01%, or less of other non-antimicrobial polypeptides.

The compositions of the invention in certain embodiments contain an antimicrobial polypeptide that is not naturally found in a human or other mammal or animal.

The compositions of the invention can include at least 1 mg (e.g., at least 5, 10, 20, 30, 40, 50, 75, 100, 150, 200, 250, 300, 400, 500, 600, 700, 800, 900, 1000 mg, or more) of antimicrobial polypeptide. Thus, for example, the compositions can include an amount of antimicrobial polypeptide equal to about 1 mg to about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints).

The compositions of the invention can include a solution that contains at least 1 mg/ml (e.g., at least 5, 10, 15, 20, 25, 30, 35, 40, 45, 50, 55, 60, 65, 70, 75, 80, 85, 90, 95, 100 mg/ml or more) of an antimicrobial polypeptide. Thus, for example, the compositions can include a solution having an antimicrobial polypeptide concentration of about 1 mg/ml to about 1000 mg/ml (e.g., about 5 mg/ml to about 900 mg/ml, about 5 mg/ml to about 800 mg/ml, about 5 mg/ml to about 700 mg/ml, about 5 mg/ml to about 600 mg/ml, about 5 mg/ml to about 500 mg/ml, about 10 mg/ml to about 500 mg/ml, about 10 mg/ml to about 400 mg/ml, about 10 mg/ml to about 300 mg/ml, about 10 mg/ml to about 250 mg/ml, about 10 mg/ml to about 200 mg/ml, about 10 mg/ml to about 150 mg/ml, about 10 mg/ml to about 100 mg/ml, about 50 mg/ml to about 500 mg/ml, about 50 mg/ml to about 400 mg/ml, about 50 mg/ml to about 300 mg/ml, about 50 mg/ml to about 250 mg/ml, about 50 mg/ml to about 200 mg/ml, about 50 mg/ml to about 150 mg/ml, about 50 mg/ml to about 100 mg/ml, about 75 mg/ml to about 500 mg/ml, about 75 mg/ml to about 400 mg/ml, about 75 mg/ml to about 300 mg/ml, about 75 mg/ml to about 250 mg/ml, about 75 mg/ml to about 200 mg/ml, about 75 mg/ml to about 150 mg/ml, about 75 mg/ml to about 100 mg/ml, about 100 mg/ml to about 500 mg/ml, about 100 mg/ml to about 400 mg/ml, about 100 mg/ml to about 300 mg/ml, about 100 mg/ml to about 250 mg/ml, about 100 mg/ml to about 200 mg/ml, about 10 mg/ml to about 150 mg/ml, or any other range containing two of the foregoing endpoints).

The compositions of the invention include pharmaceutical compositions. Such pharmaceutical compositions can comprise one or more antimicrobial polypeptides and a pharmaceutically acceptable carrier. Pharmaceutical compositions can further include an active ingredient other than an antimicrobial polypeptide of the invention. The other active ingredient can be a therapeutic/antimicrobial agent, such as a conventional antibiotic. The conventional antibiotic can have antimicrobial properties or other properties that the antimicrobial polypeptides of the invention augment or are augmented by. In certain embodiments the pharmaceutical composition includes a carrier, e.g., a carrier protein such as serum albumin (e.g., HAS, BSA, etc.), which can be purified or recombinantly produced. By mixing the antimicrobial polypeptide(s) in the pharmaceutical composition with serum album, the antimicrobial polypeptides can be effectively "loaded" onto the serum albumin, allowing a greater amount of antimicrobial polypeptide to be successfully delivered to a site of infection. The pharmaceutical compositions of the present invention can be formulated for oral administration, parenteral administration, topical administration, or the like. Compositions formulated for oral delivery can, for example, include an enteric coat, to ensure that antimicrobial peptides contained therein reach the intestine and beyond. Compositions formulated for topical delivery can be, for example, suspended in a gel or cream or infused into a bandage, to extend the duration of action of the antimicrobial peptides contained therein. Alternatively, the antimicrobial peptides of the invention can be coated on the surface of medical devices, such as surgical instruments and indwelling medical devices (e.g., pacemakers, catheters, artificial joints, and the like), as a means of preventing infection.

Methods

The antimicrobial polypeptides of the invention provide powerful tools for treating or preventing a microbial infection in a subject. Accordingly, the invention provides methods of eliminating, reducing the number of, or significantly reducing the replication of at least one microbial organism in a subject. The subject can be any animal, such as a domesticated animal (e.g., a horse, cow, pig, goat, sheep, rabbit, chicken, turkey, duck, etc.), a pet (e.g., a dog, cat, rabbit, hamster, gerbil, bird, fish, etc.), a lab animal (e.g., a mouse, rat, monkey, chimpanzee, owl, fish, etc.), a zoo animal (e.g., a gorilla, orangutan, chimpanzee, monkey, elephant, camel, zebra, boar, lion, tiger, giraffe, bear, bird, etc.), a wild animal (e.g., a deer, wolf, mountain lion, bird, etc.), or a human subject (e.g., a patient).

The antimicrobial polypeptide(s) can be administered at a dose and frequency that depends on the type of animal, the size of the animal, and the condition being treated. Typically, the antimicrobial polypeptide is administered daily (or every other day, or weekly), in an amount between about 1 mg and about 1000 mg (e.g., about 5 mg to about 900 mg, about 5 mg to about 800 mg, about 5 mg to about 700 mg, about 5 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 75 mg to about 500 mg, about 75 mg to about 400 mg, about 75 mg to about 300 mg, about 75 mg to about 250 mg, about 75 mg to about 200 mg, about 75 mg to about 150 mg, about 75 mg to about 100 mg, about 100 mg to about 500 mg, about 100 mg to about 400 mg, about 100 mg to about 300 mg, about 100 mg to about 250 mg, about 100 mg to about 200 mg, or any other range containing two of the foregoing endpoints). The daily dose can be administered once during the day, or broken up into smaller doses that are taken at multiple time points during the day. For a human (and other similarly-sized mammals), a dose of 5 mg/kg every other day can be administered. The antimicrobial polypeptide can be administered for a fixed period of time (e.g., for 2-3 weeks), at intervals (e.g., administer polypeptide for 2-3 weeks, wait 2-3 weeks, then repeat the cycle), or until such time as the microbial organism has been eliminated or significantly reduced, the symptoms of the microbial infection have been ameliorated, or the potential microbial infection risk has been reduced o eliminated (e.g., a wound has healed).

The administration of the antimicrobial polypeptides (or pharmaceutical compositions comprising such polypeptides) in conjunction with any of the foregoing methods can be performed intravenously, intraperitoneally, parenterally, orthotopically, subcutaneously, topically, nasally, orally, sublingually, intraocularly, by means of an implantable depot, using nanoparticle-based delivery systems, microneedle patch, microspheres, beads, osmotic or mechanical pumps, and/or other mechanical means.

In conjunction with any of the foregoing methods, the antimicrobial polypeptides (or pharmaceutical compositions comprising such polypeptides) can be administered in combination with another drug, e.g., an antibiotic, antiviral, antifungal, antiprotozoal, antimalarial, or a drug for treating a non-infectious disease or other condition. In certain embodiments, the other drug is one that can reduce a symptom of a disease/microbial infection (e.g., to reduce or prevent a fever, to treat or prevent nausea, etc.). In each case, the antimicrobial polypeptide can be administered prior to, at the same time as, or after the administration of the other drug.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Activity Against Planktonic Gram-Negative and Gram-Positive Bacteria

Peptides were tested against the following challenge organisms by the M11-A8E CLSI standard for Antimicrobial Susceptibility Testing of Anaerobic Bacteria: *Enterococcus faecium* ATCC 700221; *Enterobacter aerogens* ATCC 13048; *Staphylococcus aureus* MRSA ATCC 33591; *Streptococcus pneumoniae* ATCC 49619; *Pseudomonas aeruginosa* ATCC 27853; *Acinetobacter baumannii* ATCC 17978D-5; *Pseudomonas aeruginosa* ATCC 19660; and *Staphylococcus epidermidis* ATCC 51625. Sample dilutions ranged from initial sample to 1:2048. Eleven (11) concentrations were tested in duplicate on a 96 well plate by MQA Laboratories. Results are shown in Table 4 as Minimum bactericidal concentration (MBC), which is the concentration of each peptide necessary to yield 99.9% lethality for each of the eight challenge organisms. (The concentrations in Table 4 are averages of the MBC across all bacteria tested in μM).

TABLE 4

| Peptide | SEQ ID NO | Average MBC (μM) |
|---------|-----------|------------------|
| RP438   | 17        | 5.3              |
| RP444   | 23        | 7.5              |
| RP441   | 20        | 8.8              |
| RP445   | 24        | 10.4             |
| RP443   | 22        | 11.3             |
| RP442   | 21        | 15.2             |
| RP440   | 19        | 18               |
| RP439   | 18        | 18.4             |
| RP435   | 14        | 19.6             |
| RP437   | 16        | 27.4             |
| RP436   | 15        | 40.9             |

Example 2: Activity Against Biofilm Bacteria

The Minimum Biofilm Eradication Concentration (MBEC) Assay was used. MBEC values provide estimates on the concentration of an antimicrobial product required to kill biofilm bacteria. The Calgary Biofilm Device (CBD) plate was used to effect biofilm formation on a lid containing 96 pegs. Bacterial cultures were grown and diluted in Tryptic Soy Broth (TSB) to approximately $1 \times 10^7$ CFU/mL before inoculation of the CBD plate, which was then incubated for 24 hr at 35° C. on a shaker at 125 rpm.

The peg lid containing biofilm was first rinsed in PBS to remove planktonic cells prior to treatment with 2-fold serial dilutions of test articles and control overnight at 35° C. The peg lid was rinsed in PBS twice before sonication in fresh media to disrupt biofilm adhered to the pegs. The plate was then incubated overnight to evaluate growth. Bacterial quantification was performed by measuring absorbance at 650 nm (A650). By definition, A650 reading of less than 0.1 indicates biofilm eradication. Results are shown in Table 5.

TABLE 5

| | Average MBEC (µM) Peptide | | | |
|---|---|---|---|---|
| Bacteria | RP438 (SEQ ID NO: 17) | RP442 (SEQ ID NO: 21) | RP443 (SEQ ID NO: 22) | RP444 (SEQ ID NO: 23) |
| S. aureus MRSA (G+) | 12.89 | 14.68 | 7.36 | 14.41 |
| S. epidermis (G+) | 12.89 | 14.68 | 3.68 | 14.41 |
| A. baumanii (G−) | 6.45 | 1.87 | 3.68 | 3.68 |
| P. aeruginosa (G−) | 51.43 | 234.28 | 57.62 | 57.62 |

Example 3: Activity Against Biothreat Bacteria (*B. thailandensis*)

In vitro activity of the Test Articles and comparator antibiotic (ceftazidime) were tested as follows: in a sterile 96-well plate, 1×10$^5$ CFU per well of bacteria were incubated with serial dilutions of antibiotic (control) and peptide in 10 mM phosphate buffer (3 h, 37° C.). Bacterial survival was determined by serial dilution at each peptide concentration in sterile PBS. Dilutions were plated in triplicate on nutrient agar and incubated at 37° C. for 24 h; colonies were then counted to determine survival. Bacterial survival was calculated by the ratio of the number of colonies on each experimental plate to the average number of colonies in the control plates lacking any antimicrobial peptide. The antimicrobial peptide concentration required to kill 50% of *B. thailandensis* (EC50) was determined by graphing percent survival versus log of peptide concentration. EC50 was determined by fitting the data to a standard sigmoidal dose-response curve. Each experiment was performed with three replicates. Table 6 shows the EC50 results for each peptide tested and for the antibiotic Ceftazidime.

TABLE 6

| Peptide | EC50 in µM |
|---|---|
| RP438 (SEQ ID NO: 17) | 11.21 |
| RP442 (SEQ ID NO: 21) | 0.95 |
| RP443 (SEQ ID NO: 22) | 55.63 |
| RP444 (SEQ ID NO: 23) | 14.77 |
| Ceftazidime | 39.13 |

Example 4: Antibacterial and Antifungal Activity of Selected Peptides (IC50 Values)

Measurement of antimicrobial and anti-fungal activity was determined by a standard micrometer dilution method. Briefly, cells were grown overnight in media specified for each strain, and were diluted in the same media. Serial dilutions of the peptides were added to microtiter plates in a volume of 50 ul, followed by the addition of 50 ul of bacteria or fungi, 5×10$^5$ CFU/ml. Plates were incubated at 37 degrees for 24 hours and the Minimum Inhibitory Concentrations (MICs) were determined as the lowest peptide concentration that inhibited 50% of bacterial growth. Table 7 shows the IC50 in uM for each bacterial isolate tested and Table 8 shows the IC50 in uM for each fungus tested.

TABLE 7

Bacterial Cell Results

| | IC50 (in µM) Peptide | | |
|---|---|---|---|
| Bacteria | RP500 (SEQ ID NO: 25) | RP501 (SEQ ID NO: 26) | RP504 (SEQ ID NO: 27) |
| *A. baumanii* | | | |
| Isolate 6043 | 7.6 | 7.3 | 21.7 |
| Isolate 4838 | 7.6 | 29.0 | 43.3 |
| *E. coli* | | | |
| Isolate 6571 | 3.8 | 7.3 | 10.8 |
| Isolate 6572 | 3.8 | 7.3 | 10.8 |
| *E. cloaca* | | | |
| Isolate 6053 | 7.6 | 14.5 | 10.8 |
| Isolate 6054 | 7.6 | 14.5 | 21.7 |
| *Pseudomonas* | | | |
| Xen5 | 0.5 | 14.5 | 10.8 |
| *Staphylococcus* | | | |
| Xen36 | 3.8 | 14.5 | 10.8 |
| Average | 5.3 | 13.6 | 17.6 |

TABLE 8

Fungal Cell Results

| | IC50 (in uM) Peptide | | | |
|---|---|---|---|---|
| Fungus | RP504 (SEQ ID NO: 27) | RP505 (SEQ ID NO: 28) | RP507 (SEQ ID NO: 29) | RP508 (SEQ ID NO: 30) |
| *C. albicans* | | | | |
| Isolate Y-326 | 43.3 | 17.5 | 79.9 | — |
| Isolate Y-6359 | 43.3 | 8.8 | 40.0 | 38.3 |
| *C. krusei* | | | | |
| Isolate Y-27803 | 2.7 | 17.5 | 20.0 | 38.3 |
| Isolate Y-27825 | 2.7 | 17.5 | 20.0 | 38.3 |
| *C. tropicalis* | | | | |
| Isolate Y-48158 | — | 8.8 | 40.0 | 76.6 |
| Isolate Y-48166 | — | 8.8 | 40.0 | 38.3 |
| Average | 23.0 | 13.2 | 43.3 | 46.0 |

Example 5: Screening of Peptides for In Vitro Bactericidal Activity

Bacteria tested included *Burkholderia cepacia* strain Toronto (B.c.), *Porphyromonas gingivalis* strains A7436 and HG405, *Actinobacillus actinomycetemcomitans* strain A7154 (A.a.), *Fusobacterium nucleatum* strain 1594 (F.n.), *Escherichia coli* strain (E.c.), *Staphylococcus aureus* ATCC strain 29213 (S.a.), and *Pseudomonas aeruginosa* strain (P.a.). All bacteria were grown in appropriate media under appropriate atmosphere to the early exponential phase of growth. Media were inoculated with a dose of bacteria to assure a minimum of five doublings before harvesting. The cultures were washed twice in saline by centrifugation and resuspended in saline at suitable concentration. In the initial screening, all peptides were used at a final concentration of 10 µM in saline with the target bacteria at 10$^6$ CFU/ml as estimated by optical density at 660 nm. Controls were treated with an equal volume of saline. The suspensions were incubated at 37° C. in ambient atmosphere and aliquots removed temporally (0 to 2 hrs) for quantitative recovery of colony forming units. This allowed determination of the kinetics of killing of the individual peptides with the different bacterial strains. In general, there was little or no loss in viability of the various strains throughout the two-hour test period in the saline control. There was, however, significant loss in viability (>1 $\log_{10}$) in the controls of both *Fusobacterium nucleatum* and *Actinobacillus actinomycetemcomitans* within the time period, but there was no detectable reduction until after 30 minutes. Killing was considered significant if there was greater than a one-log reduction in recoverable CFU in the peptide-treated vs. the saline-treated control. Peptides that failed to kill at 10 µM were considered inactive. Any peptide that resulted in greater than two logs reduction was titrated by either two-fold, five-fold or ten-fold dilutions prior to testing with $10^6$ CFU/ml of the target bacteria. The endpoint titration is determined as the last concentration of peptide (in µM) that gives greater than two-logs reduction in recoverable CFU vs. the saline-treated control ("Two-log Reduction Concentration"). This two-log reduction concentration for SEQ ID NOs: 12 and 6 for each bacteria tested is shown in Table 9 along with the average value across all bacteria (last column).

TABLE 9

| SEQ ID NO | Two-log Reduction Concentration (in µM) Bacteria | | | | | | | | |
|---|---|---|---|---|---|---|---|---|---|
| | B.c. | A7436 | HG405 | A.a. | F.n. | E.c. | S.a. | P.a. | Ave. |
| 12 (RP-433) | 0.12 | 0.16 | 0.36 | 0.10 | 1.25 | 0.63 | 0.15 | 0.90 | 0.46 |
| 6 | 1.25 | 1.88 | 2.50 | 0.40 | 3.75 | 0.63 | 1.26 | ND | 1.67 |

Example 6: Killing of Antibiotic Resistant Bacteria

Figure 2:
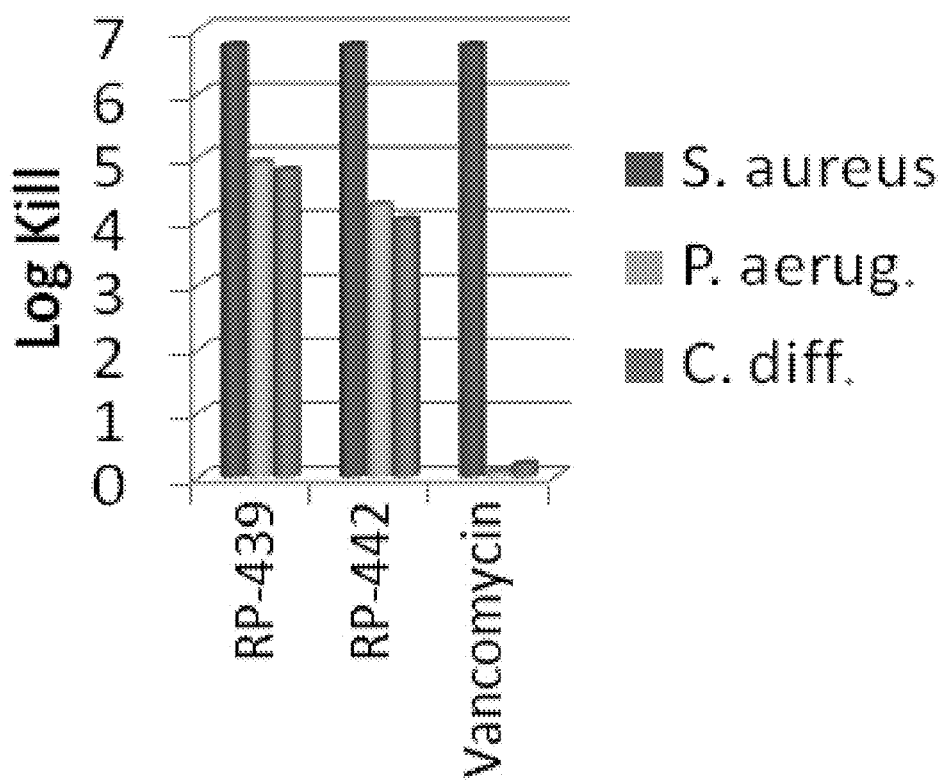
FIG. 2 shows data for the activity of two peptides of the present invention (designated "RP-439" and "RP-442"; SEQ ID NOs: 18 and 21, respectively) against select microbial organisms associated with hospital-acquired infections as compared to the antibiotic vancomycin. The organisms associated with hospital-acquired infections tested were *Staphylococcus aureus, Pseudomonas aeruginosa*, and *Clostridium difficile*.

*Staphylococcus aureus*, *Pseudomonas aeruginosa*, and *Clostridium difficile* were tested for their sensitivity to RP-439 and RP-442 (SEQ ID NOs: 18 and 21, respectively). These organisms are associated with hospital-acquired infections. The experiments were performed as described in Example 5. FIG. 2 shows results taken at 1 hour time point after addition of the indicated peptide or vancomycin. As is clear in FIG. 2, *S. aureus* was effectively killed by both peptides at a level similar to vancomycin. However, it was found that these peptides showed a broader range of efficacy than this conventional antibiotic. Specifically, RP-439 and RP-442 were effective in killing both *P. aeruginosa* and *C. difficile*, whereas vancomycin was not effective against these microbial organisms. Similar results were obtained whether the bacteria were exposed in single cell format (shown in FIG. 2) or in biofilm form (as described in the previous Examples; biofilm data for RP-442 against *S. aureus* and *P. aerugenosa* shown above; biofilm data not shown for *C. difficile* and peptide RP-439).

The results provided in the Examples demonstrate the efficacy of the antimicrobial peptides of the invention in killing a wide range of microbial organisms, including those that cause medically important human infections.

Embodiments

The following non-limiting embodiments are provided to illustrate aspects of the present invention.

1. An antimicrobial composition comprising an antimicrobial peptide, wherein the antimicrobial peptide comprises an amino acid sequence having at least 60% sequence identity to any one of SEQ ID NOs: 23, 25, 17, 12, 13, 27, 1 to 6, 8, 9, 14 to 16, 18 to 22, 24, 26, and 28 to 30.

2. The antimicrobial composition of embodiment 1, wherein the antimicrobial peptide is effective in killing at least one bacterial, fungal, or protozoal organism.

3. The antimicrobial composition of embodiment 2, wherein the organism is a species classified in a genus selected from the group consisting of: *Acinetobacter*, *Actinobacillus*, *Burkholderia*, *Candida*, *Clostridium*, *Enterobacter*, *Enterococcus*, *Escherichia*, *Fusobacterium*, *Porphyromonas*, *Pseudomonas*, *Staphylococcus*, and *Streptococcus*. In some embodiments, the organism is resistant to one or more conventional antibiotics (e.g., an MRSA organism).

4. The antimicrobial composition of embodiment 3, wherein the organism is selected from the group consisting of: *Acinetobacter baumannii*, *Actinobacillus actinomycetemcomitans*, *Burkholderia cepacia*, *Burkholderia thailandensis*, *Candida albicans*, *Candida krusei*, *Candida tropicalis*, *Clostridium difficile*, *Enterobacter aerogens*, *Enterobacter cloaca*, *Enterococcus faecium*, *Escherichia coli*, *Fusobacterium nucleatum*, *Porphyromonas gingivalis*, *Pseudomonas aeruginosa*, *Pseudomonas aeruginosa*, *Pseudomonas aeruginosa*, *Staphylococcus aureus*, *Staphylococcus aureus*, *Staphylococcus epidermidis*, and *Streptococcus pneumoniae*.

5. The antimicrobial composition of any one of embodiments 2 to 4, wherein the antimicrobial peptide is effective in killing microbes growing as a microbial biofilm.

6. The antimicrobial composition of any preceding embodiment, wherein the antimicrobial peptide comprises an amphipathic region having a cationic surface that binds to the membrane of a microbial pathogen.

7. The antimicrobial composition of any preceding embodiment, wherein the antimicrobial peptide comprises a polyproline helix structure.

8. The antimicrobial composition of any preceding embodiment, wherein the antimicrobial peptide comprises a hydrophobic tail region on the N-terminus, C-terminus, or both, wherein the hydrophobic tail region has a sequence of from 4 to 10 hydrophobic amino acids.

9. The antimicrobial composition of embodiment 8, wherein the hydrophobic tail region has the amino acid sequence set forth in SEQ ID NO: 4.

10. The antimicrobial composition of any preceding embodiment, wherein the antimicrobial peptide comprises two amphipathic regions.

11. The antimicrobial composition of embodiment 10, wherein the two amphipathic regions are joined together by a linker.

12. The antimicrobial composition of embodiment 11, wherein the linker comprises a bubble region or a beta turn.

13. The antimicrobial composition of any one of embodiments 10 to 12, wherein the two amphipathic regions form a dimer structure.

14. The antimicrobial composition of any one of embodiments 10 to 13, wherein the two amphipathic regions have the same amino acid sequence.

15. The antimicrobial composition of any one of embodiments 10 to 13, wherein the two amphipathic regions have different amino acid sequences.

16. The antimicrobial composition of any preceding embodiment, wherein the antimicrobial peptide comprises an amino acid sequence selected from the group consisting of: SEQ ID NOs: 23, 25, 17, 12, 13, 27, 1 to 6, 8, 9, 14 to 16, 18 to 22, 24, 26, 28 to 30; amino acid sequences having 5 or fewer amino acid differences from any one of SEQ ID NOs: 23, 25, 17, 12, 13, 27, 1 to 6, 8, 9, 14 to 16, 18 to 22, 24, 26, 28 to 30; and homodimers or heterodimers thereof linked by a linker.

17. A pharmaceutical composition comprising the antimicrobial composition of any one of embodiments 1 to 16 and a pharmaceutically acceptable carrier.

18. The pharmaceutical composition of embodiment 17, wherein the composition is formulated for oral administration, parenteral administration, or topical administration.

19. The pharmaceutical composition of embodiment 18, wherein the composition is formulated for oral administration and further comprises an enteric coating.

20. The pharmaceutical composition of embodiment 18, wherein the composition is formulated for topical delivery in a form selected from the group consisting of: a gel suspension, a cream, microneedle, and infusion into a bandage or topical patch.

21. The pharmaceutical composition of any one of embodiments 17 to 20, further comprising an additional bioactive agent.

22. The pharmaceutical composition of embodiment 21, wherein the additional bioactive agent is selected from the group consisting of: an antimicrobial agent, an anti-inflammatory drug, an anti-nausea drug, an anti-pain medication, and combinations thereof.

23. The pharmaceutical composition of embodiment 17, wherein the composition is formulated to be coated on the surface of an implantable medical device.

24. The pharmaceutical composition of embodiment 23, wherein the medical device is selected from the group consisting of: surgical instruments and indwelling medical devices.

25. A method of treating or preventing a microbial infection in a subject in need thereof, the method comprising administering a pharmaceutical composition according to any one of embodiments 17 to 24 to the subject.

26. The method of embodiment 25, wherein the pharmaceutical composition is administered to the subject orally, parenterally, or topically.

27. The method of embodiment 25, wherein the pharmaceutical composition is administered to the subject by applying the composition to a surface of a medical device prior to inserting the medical device into the subject.

28. The method of any one of embodiments 25 to 27, wherein the subject is selected from the group consisting of: a human, a domesticated animal, a farm animal, and a zoo animal.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

---

What is claimed:

1. An antimicrobial composition comprising an antimicrobial peptide, wherein the antimicrobial peptide comprises an amino acid sequence having at least 90% sequence identity to one of SEQ ID NOs: 3, 5, 8, 18, 22, 23 and 25-30.

2. The antimicrobial composition of claim 1, wherein the antimicrobial peptide comprises a hydrophobic tail region on the N-terminus, C-terminus, or both, and wherein the hydrophobic tail region has a sequence of from 4 to 10 hydrophobic amino acids.

3. The antimicrobial composition of claim 2, wherein the hydrophobic tail region consists of the amino acid sequence set forth in SEQ ID NO: 4.

4. The antimicrobial composition of claim 3, wherein the antimicrobial peptide comprises an amino acid sequence selected from SEQ ID NOs: 22 and 23.

5. The antimicrobial composition of claim 1, wherein the antimicrobial peptide comprises an amino acid sequence selected from SEQ ID NOs: 8, 18 and 27.

6. The antimicrobial composition of claim 1, wherein the antimicrobial peptide comprises two amphipathic regions that form a dimer.

7. The antimicrobial composition of claim 6, wherein the two amphipathic regions have the same amino acid sequence.

8. The antimicrobial composition of claim 6, wherein the two amphipathic regions have different amino acid sequences.

9. The antimicrobial composition of claim 1, wherein the antimicrobial peptide comprises an amino acid sequence having at least 95% sequence identity to one of SEQ ID NOs: 3, 5, 8, 18, 22, 23 and 25-30.

10. The antimicrobial composition of claim 1, wherein the antimicrobial peptide comprises the amino acid sequence of SEQ ID NO: 23.

11. The antimicrobial composition of claim 1, wherein the antimicrobial peptide comprises the amino acid sequence of SEQ ID NO: 22.

12. The antimicrobial composition of claim 1, wherein the antimicrobial peptide comprises an amino acid sequence selected from the group consisting of SEQ ID NOs: 3, 5, 8, 18, 22, 23 and 25-30.

13. The antimicrobial composition of claim 1, wherein the antimicrobial peptide comprises the amino acid sequence of SEQ ID NO: 27.

14. A pharmaceutical composition comprising the antimicrobial composition of claim 1 and a pharmaceutically acceptable carrier.

15. The pharmaceutical composition of claim 14, wherein the composition is formulated for oral administration, parenteral administration, or topical administration.

16. The pharmaceutical composition of claim 15, wherein the composition is formulated for oral administration and further comprises an enteric coating.

17. The pharmaceutical composition of claim 15, wherein the composition is formulated for topical delivery in a form selected from the group consisting of: a gel suspension, a cream, microneedle, and infused into a bandage or topical patch.

18. The pharmaceutical composition of claim 14, further comprising an additional bioactive agent.

19. The pharmaceutical composition of claim 18, wherein the additional bioactive agent is selected from the group consisting of: an antimicrobial agent, an anti-inflammatory drug, an anti-nausea drug, an anti-pain medication, and combinations thereof.

20. The pharmaceutical composition of claim 14, wherein the composition is formulated to be coated on the surface of an implantable medical device.

21. The pharmaceutical composition of claim 20, wherein the medical device is selected from the group consisting of: surgical instruments and indwelling medical devices.

22. An antimicrobial composition comprising an antimicrobial peptide, wherein the antimicrobial peptide comprises the amino acid sequence of SEQ ID NO: 21.

23. An antimicrobial composition comprising an antimicrobial peptide, wherein the antimicrobial peptide comprises an amino acid sequence selected from the group consisting of SEQ ID NOs: 6 and 20.

24. The antimicrobial composition of claim 23, wherein the antimicrobial peptide comprises the amino acid sequence of SEQ ID NO: 20.

25. The antimicrobial composition of claim 23, wherein the antimicrobial peptide comprises the amino acid sequence of SEQ ID NO: 6.

26. An antimicrobial composition comprising an antimicrobial peptide, wherein the antimicrobial peptide comprises the amino acid sequence of SEQ ID NO: 19.

27. A pharmaceutical composition comprising the antimicrobial composition of claim 10 and a pharmaceutically acceptable carrier.

28. The pharmaceutical composition of claim 27, wherein the composition is formulated for oral administration, parenteral administration, or topical administration.

29. The pharmaceutical composition of claim 28, wherein the composition is formulated for topical delivery in a form selected from the group consisting of: a gel suspension, a cream, microneedle, and infused into a bandage or topical patch.

30. The pharmaceutical composition of claim 27, wherein the composition is formulated to be coated on the surface of an implantable medical device.

31. The pharmaceutical composition of claim 30, wherein the medical device is selected from the group consisting of: surgical instruments and indwelling medical devices.

32. A pharmaceutical composition comprising the antimicrobial composition of claim 13 and a pharmaceutically acceptable carrier.

33. The pharmaceutical composition of claim 32, wherein the composition is formulated for oral administration, parenteral administration, or topical administration.

34. The pharmaceutical composition of claim 33, wherein the composition is formulated for topical delivery in a form selected from the group consisting of: a gel suspension, a cream, microneedle, and infused into a bandage or topical patch.

35. The pharmaceutical composition of claim 32, wherein the composition is formulated to be coated on the surface of an implantable medical device.

36. The pharmaceutical composition of claim 35, wherein the medical device is selected from the group consisting of: surgical instruments and indwelling medical devices.

* * * * *

UNITED STATES PATENT AND TRADEMARK OFFICE
CERTIFICATE OF CORRECTION

PATENT NO. : 10,017,542 B2  
APPLICATION NO. : 15/078794  
DATED : July 10, 2018  
INVENTOR(S) : Jesse Jaynes et al.

Page 1 of 1

It is certified that error appears in the above-identified patent and that said Letters Patent is hereby corrected as shown below:

In the Specification

Please replace "contract DM140274" with -- contract W81XWH-15-1-0616 -- (Column 1, Line 16).

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 30

<210> SEQ ID NO 1
<211> LENGTH: 18
<212> TYPE: PRT
<213> ORGANISM: Artificial Sequence
<220> FEATURE:
<223> OTHER INFORMATION: synthetic amino acid sequence

<400> SEQUENCE: 1

Arg Val Phe Lys Lys Ala Phe Arg Lys Phe Lys Lys Leu Phe Lys Arg
1               5                   10                  15

Ala Phe

<210> SEQ ID NO 2
<211> LENGTH: 18
<212> TYPE: PRT
<213> ORGANISM: Artificial Sequence
<220> FEATURE:
<223> OTHER INFORMATION: synthetic amino acid sequence

<400> SEQUENCE: 2

Phe Ala Arg Lys Phe Leu Lys Lys Phe Lys Arg Phe Ala Lys Lys Phe
1               5                   10                  15

Val Arg
```

```
<210> SEQ ID NO 3
<211> LENGTH: 18
<212> TYPE: PRT
<213> ORGANISM: Artificial Sequence
<220> FEATURE:
<223> OTHER INFORMATION: synthetic amino acid sequence

<400> SEQUENCE: 3

Phe Lys Arg Lys Ile Lys Ala Lys Leu Arg Phe Lys Ala Lys Val Arg
1               5                   10                  15

Leu Lys

<210> SEQ ID NO 4
<211> LENGTH: 5
<212> TYPE: PRT
<213> ORGANISM: Artificial Sequence
<220> FEATURE:
<223> OTHER INFORMATION: synthetic amino acid sequence

<400> SEQUENCE: 4

Phe Ala Phe Ala Phe
1               5

<210> SEQ ID NO 5
<211> LENGTH: 23
<212> TYPE: PRT
<213> ORGANISM: Artificial Sequence
<220> FEATURE:
<223> OTHER INFORMATION: synthetic amino acid sequence

<400> SEQUENCE: 5

Phe Ala Phe Ala Phe Arg Val Phe Lys Lys Ala Phe Arg Lys Phe Lys
1               5                   10                  15

Lys Leu Phe Lys Arg Ala Phe
                20

<210> SEQ ID NO 6
<211> LENGTH: 23
<212> TYPE: PRT
<213> ORGANISM: Artificial Sequence
<220> FEATURE:
<223> OTHER INFORMATION: synthetic amino acid sequence

<400> SEQUENCE: 6

Phe Ala Arg Lys Phe Leu Lys Lys Phe Lys Arg Phe Ala Lys Lys Phe
1               5                   10                  15

Val Arg Phe Ala Phe Ala Phe
                20

<210> SEQ ID NO 7
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 7

Cys Leu Gly Arg Phe Cys
1               5

<210> SEQ ID NO 8
<211> LENGTH: 18
<212> TYPE: PRT
<213> ORGANISM: Artificial Sequence
<220> FEATURE:
<223> OTHER INFORMATION: synthetic amino acid sequence
```

<400> SEQUENCE: 8

Lys Ile Arg Ala Lys Leu Cys Leu Gly Arg Phe Cys Ile Arg Ala Lys
1               5                   10                  15

Leu Arg

<210> SEQ ID NO 9
<211> LENGTH: 18
<212> TYPE: PRT
<213> ORGANISM: Artificial Sequence
<220> FEATURE:
<223> OTHER INFORMATION: synthetic amino acid sequence

<400> SEQUENCE: 9

Lys Ile Lys Ala Arg Leu Cys Leu Gly Lys Phe Cys Ile Lys Ala Arg
1               5                   10                  15

Leu Lys

<210> SEQ ID NO 10
<211> LENGTH: 6
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 10

Xaa Gly Pro Gly Arg Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic amino acid sequence

<400> SEQUENCE: 11

Phe Gly Pro Gly Arg Phe
1               5

<210> SEQ ID NO 12
<211> LENGTH: 50
<212> TYPE: PRT
<213> ORGANISM: Artificial Sequence
<220> FEATURE:
<223> OTHER INFORMATION: synthetic amino acid sequence

<400> SEQUENCE: 12

Phe Ala Phe Ala Phe Lys Ala Phe Lys Lys Ala Phe Lys Lys Phe Lys
1               5                   10                  15

Lys Ala Phe Lys Lys Ala Phe Gly Pro Gly Arg Phe Ala Lys Lys Phe
                20                  25                  30

Ala Lys Lys Phe Lys Lys Phe Ala Lys Phe Ala Lys Phe Ala Phe
            35                  40                  45

Ala Phe
    50

<210> SEQ ID NO 13
<211> LENGTH: 50
<212> TYPE: PRT
<213> ORGANISM: Artificial Sequence
<220> FEATURE:
<223> OTHER INFORMATION: synthetic amino acid sequence

<400> SEQUENCE: 13

Phe Ala Lys Lys Phe Ala Lys Lys Phe Lys Lys Phe Ala Lys Lys Phe
1               5                   10                  15

Ala Lys Phe Ala Phe Ala Phe Gly Pro Gly Arg Phe Ala Phe Ala Phe
                20                  25                  30

Lys Ala Phe Lys Lys Ala Phe Lys Lys Phe Lys Lys Ala Phe Lys Lys
            35                  40                  45

Ala Phe
    50

<210> SEQ ID NO 14
<211> LENGTH: 19
<212> TYPE: PRT
<213> ORGANISM: Artificial Sequence
<220> FEATURE:
<223> OTHER INFORMATION: synthetic amino acid sequence

<400> SEQUENCE: 14

Met Gly Phe Lys Leu Arg Ala Lys Ile Lys Val Arg Leu Arg Ala Lys
1               5                   10                  15

Ile Lys Leu

<210> SEQ ID NO 15
<211> LENGTH: 12
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (3)..(3)
<223> OTHER INFORMATION: Xaa is ornithine
<220> FEATURE:
<221> NAME/KEY: MISC_FEATURE
<222> LOCATION: (8)..(8)
<223> OTHER INFORMATION: Xaa is ornithine

<400> SEQUENCE: 15

Cys Val Xaa Leu Phe Pro Val Xaa Leu Phe Pro Cys
1               5                   10

<210> SEQ ID NO 16
<211> LENGTH: 16
<212> TYPE: PRT
<213> ORGANISM: Artificial Sequence
<220> FEATURE:
<223> OTHER INFORMATION: synthetic amino acid sequence

<400> SEQUENCE: 16

Cys Lys Leu Arg Phe Arg Gly Pro Gly Arg Ile Lys Val Arg Leu Cys
1               5                   10                  15

<210> SEQ ID NO 17
<211> LENGTH: 26
<212> TYPE: PRT
<213> ORGANISM: Artificial Sequence
<220> FEATURE:
<223> OTHER INFORMATION: synthetic amino acid sequence

```
<400> SEQUENCE: 17

Cys Pro Gly Phe Ala Lys Lys Phe Ala Lys Lys Phe Lys Lys Phe Ala
1               5                   10                  15

Lys Lys Phe Ala Lys Phe Ala Phe Ala Phe
            20                  25

<210> SEQ ID NO 18
<211> LENGTH: 18
<212> TYPE: PRT
<213> ORGANISM: Artificial Sequence
<220> FEATURE:
<223> OTHER INFORMATION: synthetic amino acid sequence

<400> SEQUENCE: 18

Lys Ile Arg Ala Lys Leu Cys Leu Gly Arg Phe Cys Ile Arg Ala Lys
1               5                   10                  15

Leu Arg

<210> SEQ ID NO 19
<211> LENGTH: 26
<212> TYPE: PRT
<213> ORGANISM: Artificial Sequence
<220> FEATURE:
<223> OTHER INFORMATION: synthetic amino acid sequence

<400> SEQUENCE: 19

Lys Lys Lys Pro Lys Pro Pro Tyr Leu Pro Lys Pro Lys Pro Pro Pro
1               5                   10                  15

Phe Phe Pro Pro Lys Leu Pro Pro Lys Ile
            20                  25

<210> SEQ ID NO 20
<211> LENGTH: 26
<212> TYPE: PRT
<213> ORGANISM: Artificial Sequence
<220> FEATURE:
<223> OTHER INFORMATION: synthetic amino acid sequence

<400> SEQUENCE: 20

Phe Ala Phe Ala Phe Lys Ala Phe Lys Lys Ala Phe Lys Lys Phe Lys
1               5                   10                  15

Lys Ala Phe Lys Lys Ala Phe Gly Pro Cys
            20                  25

<210> SEQ ID NO 21
<211> LENGTH: 22
<212> TYPE: PRT
<213> ORGANISM: Artificial Sequence
<220> FEATURE:
<223> OTHER INFORMATION: synthetic amino acid sequence

<400> SEQUENCE: 21

Phe Ala Phe Ala Phe Ala Phe Lys Lys Ala Phe Lys Lys Phe Lys Lys
1               5                   10                  15

Ala Phe Lys Lys Ala Phe
            20

<210> SEQ ID NO 22
<211> LENGTH: 23
<212> TYPE: PRT
<213> ORGANISM: Artificial Sequence
<220> FEATURE:
<223> OTHER INFORMATION: synthetic amino acid sequence
<220> FEATURE:
```

```
<221> NAME/KEY: MISC_FEATURE
<222> LOCATION: (6)..(6)
<223> OTHER INFORMATION: Xaa is ornithine
<220> FEATURE:
<221> NAME/KEY: MISC_FEATURE
<222> LOCATION: (9)..(10)
<223> OTHER INFORMATION: Xaa is ornithine
<220> FEATURE:
<221> NAME/KEY: MISC_FEATURE
<222> LOCATION: (13)..(14)
<223> OTHER INFORMATION: Xaa is ornithine
<220> FEATURE:
<221> NAME/KEY: MISC_FEATURE
<222> LOCATION: (16)..(17)
<223> OTHER INFORMATION: Xaa is ornithine
<220> FEATURE:
<221> NAME/KEY: MISC_FEATURE
<222> LOCATION: (20)..(21)
<223> OTHER INFORMATION: Xaa is ornithine

<400> SEQUENCE: 22

Phe Ala Phe Ala Phe Xaa Ala Phe Xaa Xaa Ala Phe Xaa Xaa Phe Xaa
1               5                   10                  15

Xaa Ala Phe Xaa Xaa Ala Phe
            20

<210> SEQ ID NO 23
<211> LENGTH: 23
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (3)..(4)
<223> OTHER INFORMATION: Xaa is ornithine
<220> FEATURE:
<221> NAME/KEY: MISC_FEATURE
<222> LOCATION: (7)..(8)
<223> OTHER INFORMATION: Xaa is ornithine
<220> FEATURE:
<221> NAME/KEY: MISC_FEATURE
<222> LOCATION: (10)..(11)
<223> OTHER INFORMATION: Xaa is ornithine
<220> FEATURE:
<221> NAME/KEY: MISC_FEATURE
<222> LOCATION: (14)..(15)
<223> OTHER INFORMATION: Xaa is ornithine
<220> FEATURE:
<221> NAME/KEY: MISC_FEATURE
<222> LOCATION: (18)..(18)
<223> OTHER INFORMATION: Xaa is ornithine

<400> SEQUENCE: 23

Phe Ala Xaa Xaa Phe Ala Xaa Xaa Phe Xaa Xaa Phe Ala Xaa Xaa Phe
1               5                   10                  15

Ala Xaa Phe Ala Phe Ala Phe
            20

<210> SEQ ID NO 24
<211> LENGTH: 22
<212> TYPE: PRT
<213> ORGANISM: Artificial Sequence
<220> FEATURE:
<223> OTHER INFORMATION: synthetic amino acid sequence

<400> SEQUENCE: 24

Phe Ala Lys Lys Phe Ala Lys Lys Phe Lys Lys Phe Ala Lys Lys Phe
1               5                   10                  15

Ala Phe Ala Phe Ala Phe
            20
```

<210> SEQ ID NO 25
<211> LENGTH: 31
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (11)..(12)
<223> OTHER INFORMATION: Xaa is ornithine
<220> FEATURE:
<221> NAME/KEY: MISC_FEATURE
<222> LOCATION: (15)..(16)
<223> OTHER INFORMATION: Xaa is ornithine
<220> FEATURE:
<221> NAME/KEY: MISC_FEATURE
<222> LOCATION: (18)..(19)
<223> OTHER INFORMATION: Xaa is ornithine
<220> FEATURE:
<221> NAME/KEY: MISC_FEATURE
<222> LOCATION: (22)..(23)
<223> OTHER INFORMATION: Xaa is ornithine
<220> FEATURE:
<221> NAME/KEY: MISC_FEATURE
<222> LOCATION: (26)..(26)
<223> OTHER INFORMATION: Xaa is ornithine

<400> SEQUENCE: 25

Arg Leu Ala Arg Ile Val Gly Gly Phe Ala Xaa Xaa Phe Ala Xaa Xaa
1               5                   10                  15

Phe Xaa Xaa Phe Ala Xaa Xaa Phe Ala Xaa Phe Ala Phe Ala Phe
            20                  25                  30

<210> SEQ ID NO 26
<211> LENGTH: 33
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (13)..(14)
<223> OTHER INFORMATION: Xaa is ornithine
<220> FEATURE:
<221> NAME/KEY: MISC_FEATURE
<222> LOCATION: (17)..(18)
<223> OTHER INFORMATION: Xaa is ornithine
<220> FEATURE:
<221> NAME/KEY: MISC_FEATURE
<222> LOCATION: (20)..(21)
<223> OTHER INFORMATION: Xaa is ornithine
<220> FEATURE:
<221> NAME/KEY: MISC_FEATURE
<222> LOCATION: (24)..(25)
<223> OTHER INFORMATION: Xaa is ornithine
<220> FEATURE:
<221> NAME/KEY: MISC_FEATURE
<222> LOCATION: (28)..(28)
<223> OTHER INFORMATION: Xaa is ornithine

<400> SEQUENCE: 26

Cys Arg Leu Ala Arg Ile Val Cys Gly Gly Phe Ala Xaa Xaa Phe Ala
1               5                   10                  15

Xaa Xaa Phe Xaa Xaa Phe Ala Xaa Xaa Phe Ala Xaa Phe Ala Phe Ala
            20                  25                  30

Phe

<210> SEQ ID NO 27
<211> LENGTH: 24
<212> TYPE: PRT

```
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (2)..(2)
<223> OTHER INFORMATION: Xaa is ornithine
<220> FEATURE:
<221> NAME/KEY: MISC_FEATURE
<222> LOCATION: (4)..(4)
<223> OTHER INFORMATION: Xaa is ornithine
<220> FEATURE:
<221> NAME/KEY: MISC_FEATURE
<222> LOCATION: (6)..(6)
<223> OTHER INFORMATION: Xaa is ornithine
<220> FEATURE:
<221> NAME/KEY: MISC_FEATURE
<222> LOCATION: (13)..(13)
<223> OTHER INFORMATION: Xaa is ornithine
<220> FEATURE:
<221> NAME/KEY: MISC_FEATURE
<222> LOCATION: (19)..(19)
<223> OTHER INFORMATION: Xaa is ornithine
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (23)..(23)
<223> OTHER INFORMATION: Xaa is ornithine

<400> SEQUENCE: 27

Phe Xaa Ile Xaa Ala Xaa Leu Gly Gly Cys Leu Gly Xaa Phe Cys Gly
1               5                   10                  15

Gly Ile Xaa Ala Xaa Leu Xaa Phe
            20

<210> SEQ ID NO 28
<211> LENGTH: 26
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (1)..(1)
<223> OTHER INFORMATION: Xaa is ornithine
<220> FEATURE:
<221> NAME/KEY: MISC_FEATURE
<222> LOCATION: (3)..(3)
<223> OTHER INFORMATION: Xaa is ornithine
<220> FEATURE:
<221> NAME/KEY: MISC_FEATURE
<222> LOCATION: (11)..(11)
<223> OTHER INFORMATION: Xaa is ornithine
<220> FEATURE:
<221> NAME/KEY: MISC_FEATURE
<222> LOCATION: (13)..(16)
<223> OTHER INFORMATION: Xaa is ornithine
<220> FEATURE:
<221> NAME/KEY: MISC_FEATURE
<222> LOCATION: (18)..(18)
<223> OTHER INFORMATION: Xaa is ornithine
<220> FEATURE:
<221> NAME/KEY: MISC_FEATURE
<222> LOCATION: (20)..(22)
<223> OTHER INFORMATION: Xaa is ornithine
<220> FEATURE:
<221> NAME/KEY: MISC_FEATURE
<222> LOCATION: (26)..(26)
<223> OTHER INFORMATION: Xaa is ornithine
```

```
<400> SEQUENCE: 28

Xaa Leu Xaa Ser Leu Leu Lys Thr Leu Ser Xaa Ala Xaa Xaa Xaa Xaa
1               5                   10                  15

Leu Xaa Thr Xaa Xaa Xaa Ala Ile Ser Xaa
            20                  25

<210> SEQ ID NO 29
<211> LENGTH: 27
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (7)..(9)
<223> OTHER INFORMATION: Xaa is ornithine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (14)..(14)
<223> OTHER INFORMATION: Xaa is ornithine
<220> FEATURE:
<221> NAME/KEY: MISC_FEATURE
<222> LOCATION: (16)..(16)
<223> OTHER INFORMATION: Xaa is ornithine

<400> SEQUENCE: 29

Ala Leu Trp Met Thr Leu Xaa Xaa Xaa Val Leu Xaa Ala Xaa Ala Xaa
1               5                   10                  15

Ala Leu Asn Ala Val Leu Val Gly Ala Asn Ala
            20                  25

<210> SEQ ID NO 30
<211> LENGTH: 27
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MISC_FEATURE
<222> LOCATION: (7)..(9)
<223> OTHER INFORMATION: Xaa is ornithine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (14)..(14)
<223> OTHER INFORMATION: Xaa is ornithine
<220> FEATURE:
<221> NAME/KEY: MISC_FEATURE
<222> LOCATION: (16)..(16)
<223> OTHER INFORMATION: Xaa is ornithine

<400> SEQUENCE: 30

Ala Phe Ala Phe Thr Ala Xaa Xaa Xaa Phe Ala Xaa Phe Xaa Ala Xaa
1               5                   10                  15

Phe Ala Asn Phe Ala Phe Ala Gly Phe Asn Ala
            20                  25
```